United States Patent [19]
Zanini-Fisher et al.

[11] Patent Number: 5,451,371
[45] Date of Patent: Sep. 19, 1995

[54] HIGH-SENSITIVITY, SILICON-BASED, MICROCALORIMETRIC GAS SENSOR

[75] Inventors: Margherita Zanini-Fisher, Bloomfield Township; Jacobus H. Visser, Southfield, both of Mich.

[73] Assignee: Ford Motor Company, Dearborn, Mich.

[21] Appl. No.: 257,606

[22] Filed: Jun. 9, 1994

[51] Int. Cl.6 .................. G01K 17/00; G01N 25/20
[52] U.S. Cl. ........................ 422/51; 422/95; 374/31; 374/37; 431/12; 431/89; 431/76; 60/602; 60/273; 204/153.1; 204/424
[58] Field of Search .............. 422/95, 51; 374/31, 374/37; 73/25.03; 431/12, 89, 76; 60/602, 273, 285; 204/424, 153.1

[56] References Cited

U.S. PATENT DOCUMENTS

| | | | |
|---|---|---|---|
| 4,329,873 | 5/1982 | Maeda | 73/190 |
| 4,329,874 | 5/1982 | Maeda | 73/190 |
| 4,337,654 | 7/1982 | Austin et al. | 73/190 |
| 4,706,493 | 11/1987 | Chang et al. | 73/23 |
| 4,771,271 | 9/1988 | Zanini-Fisher | 340/620 |
| 4,914,742 | 4/1990 | Higashi et al. | 357/26 |
| 5,006,421 | 4/1991 | Yang et al. | 428/641 |
| 5,012,432 | 4/1991 | Stetter et al. | 364/557 |
| 5,204,262 | 4/1993 | Meiering et al. | 435/291 |
| 5,231,878 | 8/1993 | Zanini-Fisher et al. | 73/204.26 |
| 5,250,169 | 10/1993 | Logothetis et al. | 204/424 |
| 5,265,417 | 11/1993 | Visser et al. | 60/274 |
| 5,281,313 | 1/1994 | Visser et al. | 204/153.1 |
| 5,310,335 | 5/1994 | van Bukum | 431/12 |
| 5,331,845 | 7/1994 | Bals et al. | 73/61.43 |

OTHER PUBLICATIONS

"The Si Planar Pellistor: A Low-Power Pellistor Sensor In Si Thin-Film Technology", M. Gall, Sensors and Actuators B, 4 (1991), pp. 533-538.

"A Low Power Integrated Catalytic Gas Sensor", P. Krebs et al, Sensors and Actuators B, 12 (1993), pp. 1-4.

*Primary Examiner*—Robert J. Warden
*Assistant Examiner*—N. Bhat
*Attorney, Agent, or Firm*—Roger L. May; Peter Abolins

[57] ABSTRACT

A gas sensor for measuring gas constituents, particularly exhaust gas constituents for an internal combustion engine, comprising a pair of polysilicon plates, each plate supporting a pair of resistors, one serving as a heater and the other as a thermometer, one plate being coated with a catalyst to promote combustion of unburned combustible gas constituents, wherein provision is made for reducing temperature gradients across the plates and for effecting temperature uniformity of the catalyst while maintaining a high degree of structural integrity.

5 Claims, 3 Drawing Sheets

HIGH-SENSITIVITY, SILICON-BASED, MICROCALORIMETRIC GAS SENSOR

TECHNICAL FIELD

The invention relates to electronic controls, particularly internal combustion engine controls and engine diagnostic systems, and to improvements in a catalytic microcalorimeter for detecting gas constituents.

BACKGROUND OF THE INVENTION

Electronic engine control and diagnostic strategies for internal combustion engines for automotive vehicles require sensors for detecting and measuring engine operating variables and for developing appropriate sensor inputs for a microprocessor controller that responds to the variables by calculating air/fuel ratios and engine ignition timing for optimum engine performance and fuel economy. These known engine control strategies may rely on sensors to detect combustible exhaust gas constituents and to develop a signal that may be used to quantify those constituents, even in low concentrations such as 10 ppm.

Calorimeters, which are representative of one class of these sensors, may be used to measure the combustible gas concentrations by detecting and measuring temperature rise produced by the heat of combustion of a combustible constituent as it reacts with a catalyst located on a wire thermometer that forms a part of the sensor. A well known calorimetric sensor that is commercially available is the Pellistor, which consists of a ceramic body, impregnated with a noble metal catalyst, and a platinum resistance thermometer embedded in it. In order to compensate for ambient temperature fluctuations in the exhaust gas stream, a pair of sensor elements is used in tandem so that the increase in temperature of combustion of the flammable constituents is measured relative to a reference temperature, which is the exhaust gas temperature in an internal combustion engine environment. The reference temperature and the increase in temperature due to oxidation of the combustible constituents are measured independently by the paired elements, only one of which is influenced by the catalyst. The temperature is measured by resistors on each of the two elements. The resistance value of each resistor can be used as an indication of the temperature of that element.

Engine exhaust gases typically consist of a mixture of combustible gases including various hydrocarbons, carbon monoxide and hydrogen. Calorimetric gas sensors have different sensitivities to these combustible gases according to the characteristics of the catalyst and the operating conditions as well as other factors.

Catalytic calorimetric gas sensors may include electric heaters adjacent the temperature sensing resistance on a common substrate so that the operating temperature for the sensor elements may be kept higher than the temperature of the exhaust gas stream. The sensor output is roughly proportional to the number of carbon atoms in a molecule of a particular gas constituent because the heat of combustion for a hydrocarbon is roughly proportional to the carbon content of its molecules. It is possible, for example, to detect hydrocarbons in the exhaust gas that may contain carbon monoxide as well as other constituents since hydrocarbon molecules contain more carbon atoms.

An example of a calorimetric gas sensor based on silicon is described in a publication entitled "*Sensors and Actuators*", by M. Gall, published in 1991 by Elsevier Sequoia, The Netherlands, pp. 533–538. This publication describes a metallic resistor that serves as a heater and a temperature sensor. The sensor element includes a silicon frame holding a silicon nitride membrane. The membrane is obtained by selectively etching the underlying bulk silicon with a potassium hydroxide (KOH) solution. The metallic material of the resistor is deposited by evaporation to form a metallic layer on one side of the silicon nitride layer, and photolithography and etching are used to shape the metallic layer. The silicon nitride layer serves as a thermal insulator between the sensor metallic resistor and the silicon material. If compensation for environmental temperature fluctuations is desired, dual sensor elements can be used to establish a reference temperature in the exhaust gas stream. Micromachining techniques are used in fabricating this prior art device to shape the silicon during the manufacture of the paired elements. Concentration of combustible exhaust gas constituents then can be measured by detecting the temperature difference between the paired elements.

Reference patent U.S. Pat. No. 5,265,417 describes a catalytic calorimetric gas sensor to detect hydrocarbons in the vehicle exhaust. It comprises a silicon frame on which is mounted paired sensor elements, each element comprising a membrane on which is mounted resistor elements. One resistor element is used to measure the temperature of the surrounding gas. The other element includes a catalytic layer deposited on a dielectric layer that covers both resistors. The resistor for the element that contains a catalyst measures the temperature rise generated by the oxidation of the combustible gases as in the Gall device mentioned above. The membrane portion that supports one element is thermally isolated from the membrane portion that supports the other element. This thermal isolation is achieved because of the low thermal conductivity of the membrane portions and the ability of the silicon substrate to act as a heat sink.

The membranes of the device described in the '417 patent, unlike other prior art designs, comprise a composite of silicon nitride and silicon oxide layers to compensate in part for residual stresses and to obtain thicker, more robust substrates.

BRIEF DESCRIPTION OF THE INVENTION

The improved gas sensor of our invention makes it possible to achieve high sensitivity with improved reliability. This is accomplished by incorporating mechanically stable, robust, polysilicon plates that support the paired resistors of the sensor, one of the plates also supporting a thick catalyst layer. It is characterized by a reduced temperature gradient across the plates that support the resistors. It is characterized also by its durability in the harsh environment of an engine exhaust system where it is subjected to vibration, particle impingement and thermal shock.

Each of the paired elements of the sensor includes long, strategically-shaped, polysilicon arms that support the resistors and the substrate for the resistors, thereby reducing heat conduction to a surrounding silicon frame. Each of the paired elements of the sensor includes a low-power heating element to raise the temperature of the paired elements above the temperature of the exhaust gas stream. By using polysilicon, which has high thermal conductivity, and by positioning the heater of each sensor element along the periphery of the sensor element, temperature gradients are minimized.

The support for the catalyst and the resistors is the polysilicon structure. A silicon nitride encapsulation is applied to the polysilicon structure for protection during the fabrication of the paired sensing elements. Backetching isolates the polysilicon plate from the silicon frame surrounding the paired elements of the sensor. The polysilicon elements can be accurately micromachined using reactive ion etching (RIE), a well known process, thereby adapting the process to high volume manufacturing. Further, the size of the sensing elements can be made larger than the corresponding elements of prior art sensors that may comprise more fragile membrane structures made of dielectric films.

The etching process isolates the sensing elements by providing through openings to the back surface of the sensor. The openings provide thermal isolation of the sensing elements and permit the reactants to diffuse through the sensor to the back surface. Therefore, the sensitivity can be increased by depositing the catalyst both on the top and bottom surfaces of the sensor plate.

PARTICULAR DESCRIPTION OF THE INVENTION

Figure 1:
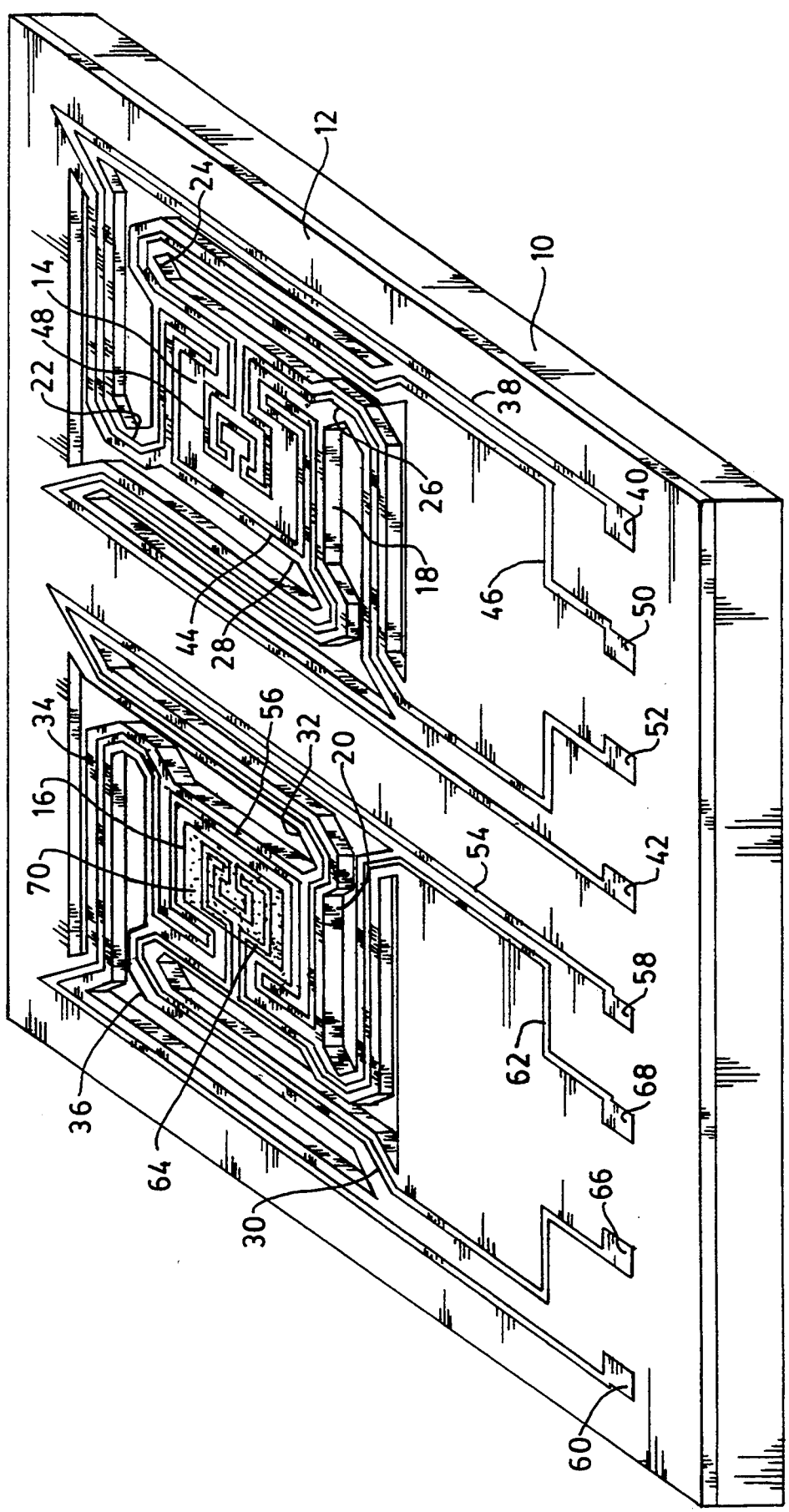
FIG. 1 is an isometric view of a microcalorimeter including polysilicon plates supported on a bulk silicon frame with metal resistors, such as platinum resistors, that serve as heaters and temperature sensing elements.

In FIG. 1, we have shown a sensor comprising a bulk silicon frame 10 and a polysilicon layer 12 attached to one side of the frame 10. Located within the boundaries of the polysilicon layer are two polysilicon plates 14 and 16. These are located in openings 18 and 20, respectively, in layer 12. Plate 14 is held in place within the opening 18 by four polysilicon arms 22, 24, 26 and 28 extending from the polysilicon layer 12. The arms are integral with layer 12.

The polysilicon plate 16 of the companion sensor is suspended in opening 20 and is held in place by four polysilicon arms shown at 30, 32, 34 and 36. These correspond to the polysilicon arms for the plate 14.

Platinum resistors are deposited on the polysilicon layer 12. Platinum conductor resistor 38 forms a heater resistance element and is provided with a heater terminal 40. A terminal 42 for the heater resistance element 38 is located also on the polysilicon layer. The resistance element 38 follows a circuitous path around the holes or openings for the sensor element plate 14 and over the sensor plate supporting arms 22 and 28. The mid-region of the resistor 38 surrounds the periphery of the plate 14, as shown at 44. The mid-region 44 of the resistor thus forms a heater element circuit between terminals 40 and 42.

A temperature-sensing resistance in the form of a metallic resistor, preferably a platinum resistor, is shown at 46. Resistor 46 extends over the arm 26. The intermediate portion of the resistor 46 is located on the inboard region of the plate 14, as shown at 48. The portion 48 thus forms a part of a complete circuit between resistor terminal 50 and resistor terminal 52 carried on the polysilicon layer 12.

The polysilicon plate 16 of the companion sensor element also has a heater resistor 54 with an intermediate portion 56 that surrounds the periphery of the plate 16. Intermediate portion 56 forms a part of a complete heater resistance circuit for the resistor 54 extending from heater terminal 58 to heater terminal 60.

The central region of the plate 16 carries intermediate portion 64 of resistor 62. The sensor resistor terminals for the resistor 62 are shown at 66 an 68. These correspond to terminals 50 and 52 of the companion sensor element.

A catalyst layer 70 is deposited on the polysilicon plate 16. No catalyst, however, is applied to the companion polysilicon plate 14.

It is thus seen that each sensor plate supports two platinum resistors. Resistors 38 and 54 serve as heaters, and the resistors 46 and 62 serve as thermometers. The location of the heater pattern at the periphery of the plates, with the thermometer pattern at the central part of each of the plates, provides uniform heat distribution for each of the plates. The high thermal conductivity of the polysilicon material compensates for thermal energy loss to the ambient gases, thus minimizing the temperature drop at the center of each of the plates. The resistance of the temperature sensing conductor is preferably ten times larger than that of the electrical interconnects that are provided by extending the platinum resistor material on the four polysilicon arms for each of the sensor element plates.

As seen in FIGS. 2A through 2F, the plates and the platinum resistors are covered by a layer of silicon nitride for passivation with the exception of the terminals, where electrical contact can be established by wire bonding.

Figure 2A:
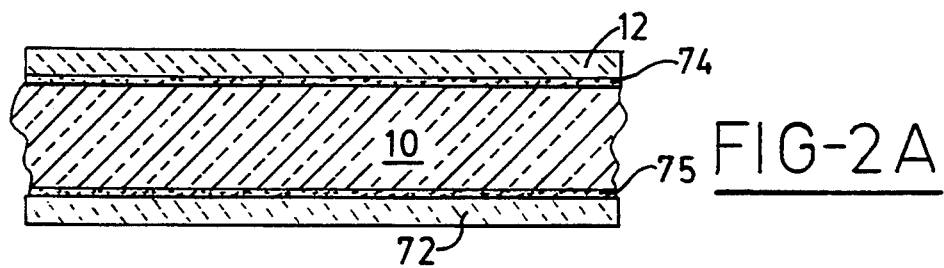
FIG. 2A is a schematic cross-sectional view of the polysilicon plate, the silicon frame and the silicon nitride layer between the silicon and the polysilicon, which are assembled in earlier steps of the fabrication process.

Referring next to FIGS. 2A through 2F, we have illustrated the various fabrication steps that are carried out in the manufacture of the sensor. FIG. 2A shows the starting materials, which comprise a bulk silicon frame 10. A polysilicon layer 12 is deposited on top of the silicon frame 10, and a corresponding layer 72 is deposited on the other side of the frame 10. As indicated also in FIG. 2A, the frame 10 is passivated on both sides by a silicon nitride layer 74 and by a silicon nitride layer 75. The thickness of the silicon nitride may be about 1000 Å. The polysilicon layers 12 and 72 may be approximately 2 microns in thickness. The polysilicon is deposited using a standard low-temperature deposition process which creates a low residual stress body or plate. Each of the plates 14 and 16 may be 800 microns or more in width, and the supporting arms may be about 40 microns or less in width.

Figure 2B:
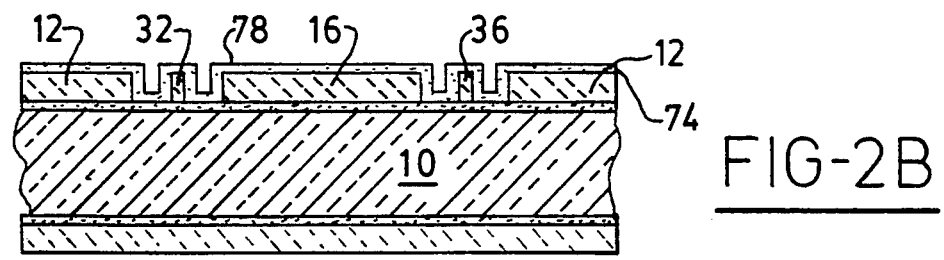
FIG. 2B is a schematic cross-sectional view of the components of the sensor element after the second step in the fabrication process involving polysilicon patterning and a passivation of silicon nitride.
Figure 2C:
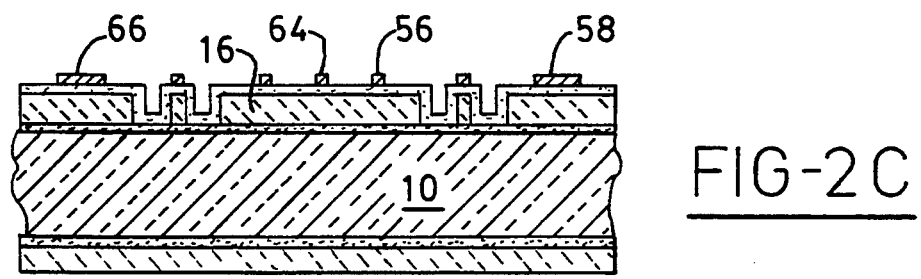
FIG. 2C is a schematic cross-sectional view of the components of the sensor during a third step in the fabrication process involving platinum deposition and patterning.

The plate 16 indicated in FIG. 2B and the arms 36 and 32 illustrated in FIG. 2B are delineated by photolithography and by selective plasma etching. The etching removes the polysilicon material, but it only partially removes the underlying silicon nitride 74. Following the etching process, the structure illustrated in FIG. 2B is passivated by applying a silicon nitride layer 78 over the plate 16 and the polysilicon 12. This layer 78 also covers the arms 32 and 36 as well as the arms that are not illustrated in the cross-sectional view of FIG. 2B.

The supporting arms for the plates are made purposely in a circuitous path to increase their lengths, thus minimizing thermal conduction to the silicon frame. We do not intend to restrict the scope of our invention, however, to a sensor having arms of any particular length or shape.

After the layer 78 is applied, a metal film, preferably a platinum film, preferably 1000 Å thick, is deposited using a well known electron beam deposition process or a sputter deposition process. The metal film is patterned by a conventional photolithography technique. If desired, a 100 Å film of titanium or chromium can be deposited before the platinum is deposited since titanium and chromium act as an adhesion promoter.

After the patterned metal film is applied, it is wet-etched, thus defining the heater and temperature sensing conductors 56 and 64, respectively. The resistors for the heater and the temperature sensor are entirely on the upper plane of the silicon nitride layer for each plate 16 and for layer 74. This prevents discontinuities that would be produced if the metal were to be deposited on different planes. Variances in electrical resistance for the metal patterns can be minimized in this way. High temperature annealing in nitrogen, typically at 600° for two hours, may be used to stabilize the resistance and to stabilize the temperature coefficient of resistance (TCR) of the conductors.

Figure 2D:
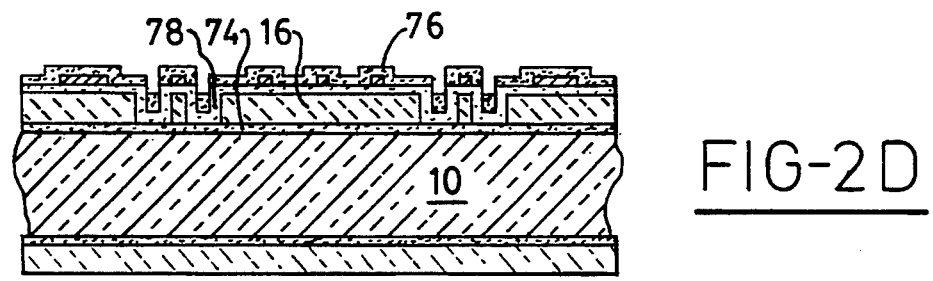
FIG. 2D is a schematic cross-sectional view of the components of the sensor during a fourth fabrication step involving a passivation layer of silicon nitride.
Figure 2E:
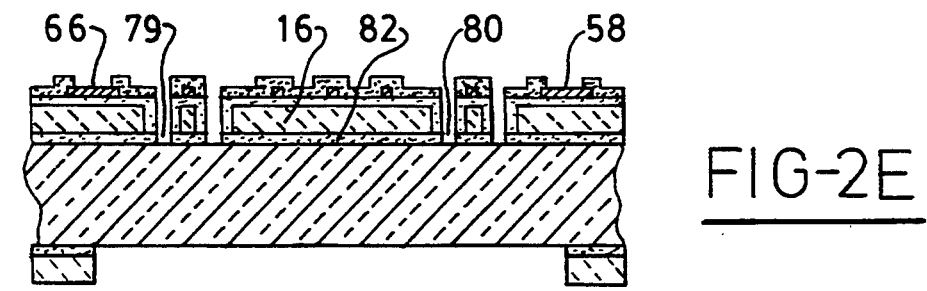
FIG. 2E illustrates the fifth step in the fabrication process, which involves selective etching of the passivation applied in the step illustrated in FIG. 2D.

Another layer of silicon nitride then is applied to the top of the plate to passivate the platinum resistors, as shown at 76 in FIG. 2D. This passivation is removed at the contact pads, as shown in FIG. 2E at 58 and 66. It is removed by lithography and plasma etching using SF6 material, a well known plasma etching compound.

The narrow openings shown at 79 and 80 in FIG. 2E are created as the silicon nitride layers at those regions identified by reference numerals 74, 76 and 78 are removed by plasma etching, thereby exposing the silicon substrate 10 in the region of the openings 79 and 80. An opening through layers 72 and 75 on the other side of the wafer or plate is also provided using photolithography and plasma etching. The bulk silicon of the substrate 10 is wet etched in potassium hydroxide (KOH) until the polysilicon plates and the arms protected by the nitride layers are entirely released. This is illustrated in the cross-sectional view of FIG. 2F.

Figure 2F:
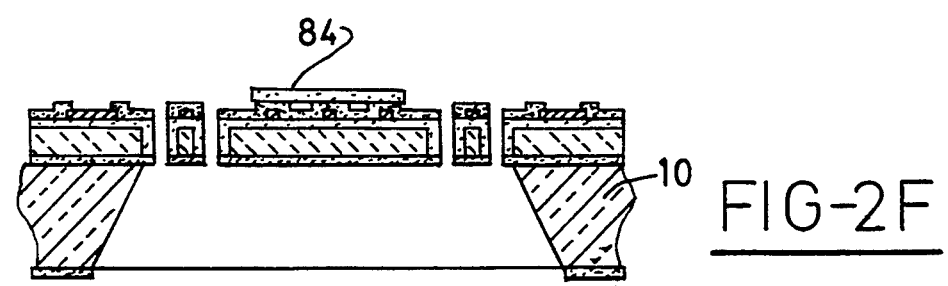
FIG. 2F is a schematic cross-sectional view of a finished sensor following a deep etch of the silicon base.

A catalyst material can be applied as shown in FIG. 2F at 84 to form the layer 70 shown in FIG. 1. The catalyst material can be a layer of noble metal, such as platinum or palladium, deposited through a shadow mask. A preferred method would involve the use of a powder slurry impregnated with a catalyst or a sol-gel solution with a catalyst. A controlled volume of the sol-gel solution, if that is the deposition method used, can be dripped over the plate with a micro syringe. Because of the presence of the polysilicon arms and the openings in the surrounding nitride, the area wetted by the solution is defined by the plate itself. The amount of catalyst deposited on the plate thus can be accurately controlled. The solvent can be removed by heating.

The catalyst also can be deposited on the back side of the plate 16 with the same deposition technique used to coat the top side. In this way, the active area of the sensor is doubled because the combustible molecules in the gas in an exhaust gas environment can diffuse through the openings at either side of the polysilicon arms to the back side of the plate. This is a further advantage of our invention over prior art constructions that use a membrane for supporting the resistor elements and the catalyst without any provision for making the underside of the membrane and the resistors accessible to combustible gases.

Another advantage inherent in our design that is not realized in prior art devices results from the use of support plates of low residual stresses. These can be easily fabricated using polysilicon. The plates thus are capable of withstanding thermal cycling without deterioration.

For purposes of this description, we have shown in FIGS. 2A through 2F the process steps for fabricating the sensor plate 16. The process for fabricating the sensor plate 14 would be the same as that described for sensor plate 16 except that the step of applying a catalyst to sensor plate 14 is not carried out.

Figure 3:
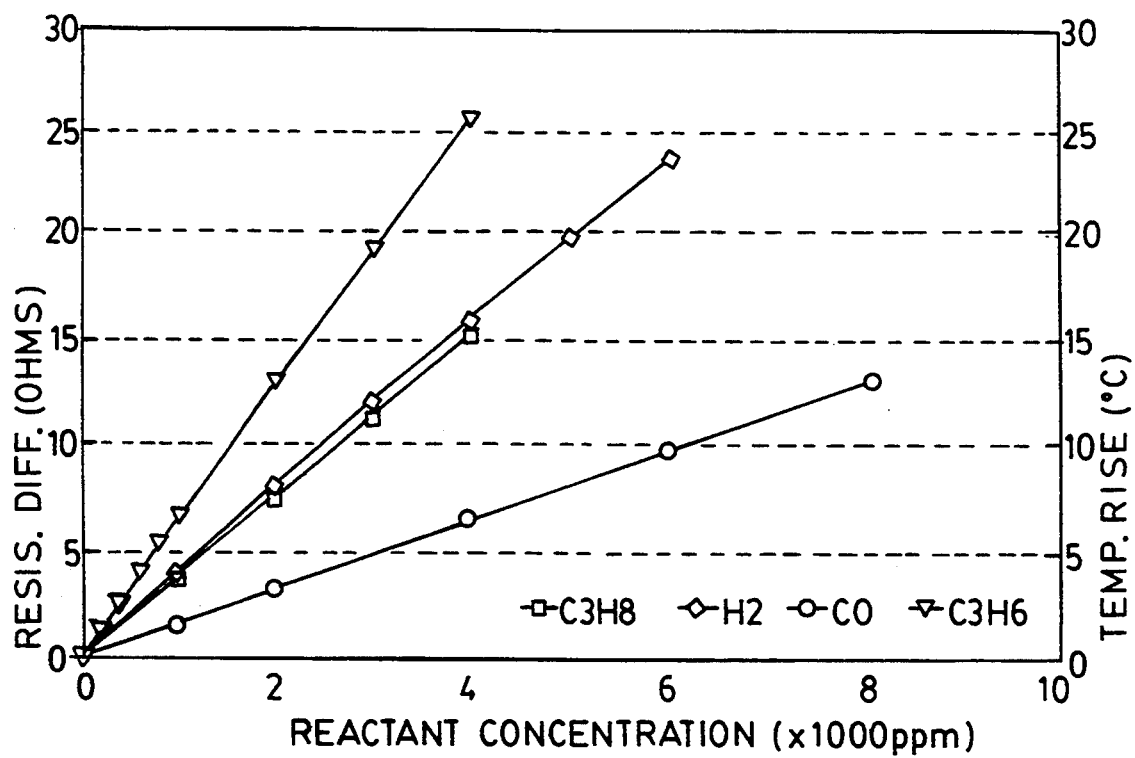
FIG. 3 is a graph showing the relationship between the resistance difference of the platinum resistors in the active and in the reference temperature sensing elements plotted as a function of four different combustible gas concentrations by volume, together with the corresponding average temperature rise produced by the reaction of each of the gases.

FIG. 3 shows the functional relationship between the concentration of various gases in the gas flow passing over the sensor and the resistance difference of the two temperature sensing resistors. The active sensing resistor and the reference sensing resistor can be connected in a Wheatstone bridge configuration to two external resistors, approximately equal in value to the resistance of the reference resistor. Thus, the rise in temperature generated by the reaction of the combustible gases on the catalyst can be derived from the bridge offset voltage, knowing the initial resistance values.

The temperature rise that produces the change in resistance for each of the gases in FIG. 3 is indicated on the right-hand ordinate of the plot. The temperature change is determined from the change in the resistance in the thermometer resistor and its previously measured temperature coefficient of resistance. The resistance of the two resistors can be represented by the following equations:

$$R_{catalytic} = R_0[1 + \alpha(T + \Delta T_{comb})]$$

$$R_{reference} = R_0[1 + \alpha T]$$

In these equations, $R_0$ is the resistance at 0° C., $\alpha$ is the temperature coefficient of resistance, T is the temperature of operation in degrees C, and $\Delta T_{comb}$ is the rise in temperature caused by the oxidation of the combustible gases on the catalytic layer. The two equations can be solved for $\Delta T_{comb}$ as follows:

$$\Delta T_{comb} = (R_{catalytic} - R_{reference})/\alpha R_0 \Delta R/\alpha R_0$$

As mentioned above, the underlying silicon nitride is partially removed in the process steps described in FIG. 2B using photolithography and selective plasma etching. These are well known techniques. Reference may be made, for example, to a text by Roy A. Cole Colclaser entitled "*Microelectronics Processing and Device Design*", published by John Wiley and Sons in 1980, Chapter 2. Various techniques can be used to apply a platinum film. Preferably, a film about 100 nm thick can be applied by a sputtering deposition process in argon after an ion milling step, the latter removing approximately 20 nm of the top silicon nitride film to improve adhesion of the platinum to the substrate. If desired, a film of titanium/platinum composition consisting of a 10 nm titanium layer and a 100 nm platinum layer can be applied using an electron beam deposition process.

The resistors are delineated by lithography and wet etching, as mentioned above. They then may be annealed at 600° C. in nitrogen to stabilize their resistances and temperature coefficients. The sensor plates then can be coated as mentioned above, which is followed by annealing at about 500° C. Further information on sputtering and other processing steps related to the application of the catalyst can be found in the reference publication by Roy Colclaser in Chapter 6.

During the process step described with reference to FIG. 2F, the bulk silicon material is etched. The silicon nitride coating 74, which is applied in the processing steps described with reference to the FIGS. 2A and 2B, protects the polysilicon plate 16 from being etched during the final etching operation for the bulk silicon material using potassium hydroxide.

The foregoing detailed description of a preferred embodiment of our invention is intended to illustrate the inventive features of the invention. It will be recognized by persons skilled in the art, however, that modifications, additions and substitutions may be made in the embodiment described without departing from the scope of the invention.

Having described a preferred embodiment of our invention, what we claim and desire to secure by U.S. Letters Patent is:

We claim:

1. A microcalorimeter to detect concentration of combustible gases in the exhaust gas of an internal combustion engine comprising a pair of temperature sensing elements, each element having a polysilicon plate, a silicon frame, at least one cavity in said frame, said polysilicon plate being supported by said frame, each plate being disposed over a frame cavity;

a polysilicon layer mounted over said base and surrounding said plates;

polysilicon support arms joining said plates to said polysilicon layer thereby supporting said plates and positioning them to define gas flow passages through said sensor and to thermally isolate said plates from said layer;

electrical resistors on each plate defining a resistance thermometer and a heater resistor; and catalyst material disposed on at least one side of one of said plates whereby the heat of combustion of said combustible gases can be detected.

2. The microcalorimeter as set forth in claim 1 wherein said resistors are mounted on said polysilicon layer and extend over said support arms to one surface of each of said polysilicon plates, said heater resistor for each plates surrounding said resistance thermometer for each plate whereby each sensor element is uniformly heated.

3. The microcalorimeter as set forth in claim 1 wherein said sensor support and said planar bodies are covered with a silicon nitride passivation.

4. The microcalorimeter set forth in claim 3 wherein said resistors and said support are covered with a common silicon nitride passivation.

5. The microcalorimeter as set forth in claim 1 wherein said plates and said polysilicon layer are covered with a silicon nitride layer, said silicon nitride layer being disposed between said polysilicon layer and said silicon frame.

* * * * *